United States Patent
Piomelli et al.

(10) Patent No.: US 10,363,237 B2
(45) Date of Patent: Jul. 30, 2019

(54) COMPOSITIONS AND METHODS OF INHIBITING N-ACYLETHANOLAMINE-HYDROLYZING ACID AMIDASE

(71) Applicants: The Regents of the University of California, Oakland, CA (US); Universita Degli Studi Di Urbino "Carlo Bo", Urbino (IT); Universita Degli Studi Di Parma, Parma (IT)

(72) Inventors: Daniele Piomelli, Irvine, CA (US); Giorgio Tarzia, Petriano (IT); Marco Mor, Ghedi (IT); Andrea Duranti, Urbino (IT); Andrea Tontini, Pesaro (IT)

(73) Assignees: The Regents of the University of California, Oakland, CA (US); Universita Degli Studi Di Urbino "Carlo Bo", Urbino (IT); Universita Degli Studi Di Parma, Parma (IT)

(*) Notice: Subject to any disclaimer, the term of this patent is extended or adjusted under 35 U.S.C. 154(b) by 0 days.

(21) Appl. No.: 15/072,194

(22) Filed: Mar. 16, 2016

(65) Prior Publication Data

US 2016/0256432 A1    Sep. 8, 2016

Related U.S. Application Data

(60) Division of application No. 13/898,225, filed on May 20, 2013, now Pat. No. 9,321,743, which is a continuation of application No. 12/678,060, filed as application No. PCT/US2008/079621 on Oct. 10, 2008, now abandoned.

(60) Provisional application No. 60/979,304, filed on Oct. 11, 2007.

(51) Int. Cl.
| | |
|---|---|
| *A61K 31/337* | (2006.01) |
| *A61K 31/165* | (2006.01) |
| *A61K 31/195* | (2006.01) |
| *A61K 31/365* | (2006.01) |
| *C07D 305/10* | (2006.01) |

(52) U.S. Cl.
CPC .......... *A61K 31/337* (2013.01); *A61K 31/165* (2013.01); *A61K 31/195* (2013.01); *A61K 31/365* (2013.01); *C07D 305/10* (2013.01)

(58) Field of Classification Search
CPC .. A61K 31/337; A61K 31/365; A61K 31/165; A61K 31/195
USPC .......................................... 514/175, 210.02
See application file for complete search history.

(56) References Cited

U.S. PATENT DOCUMENTS

| | | |
|---|---|---|
| 4,207,234 A | 6/1980 | Kamiya et al. |
| 4,550,105 A | 10/1985 | Matsuo et al. |
| 4,584,132 A | 4/1986 | Albrecht |
| 4,665,171 A | 5/1987 | Evans et al. |
| 4,683,303 A | 7/1987 | Pfaendler |
| 4,831,130 A | 5/1989 | Albrecht et al. |
| 4,870,169 A | 9/1989 | Evans et al. |
| 4,931,556 A | 6/1990 | Boyer et al. |
| 5,137,884 A | 8/1992 | Andrus et al. |
| 5,260,310 A | 11/1993 | Derungs et al. |
| 5,646,275 A | 7/1997 | Gardner et al. |
| 5,962,012 A | 10/1999 | Lin et al. |
| 6,261,595 B1 | 7/2001 | Stanley et al. |
| 6,358,978 B1 | 3/2002 | Ritzeler et al. |
| 9,321,743 B2 | 4/2016 | Piomelli et al. |
| 9,353,075 B2 | 5/2016 | Piomelli et al. |
| 9,828,338 B2 | 11/2017 | Piomelli et al. |
| 9,908,848 B2 | 3/2018 | Piomelli et al. |
| 2005/0131032 A1 | 6/2005 | Sit et al. |
| 2006/0281778 A1 | 12/2006 | Tagat et al. |
| 2007/0155747 A1 | 7/2007 | Dasse et al. |
| 2008/0050336 A1 | 2/2008 | Bachand et al. |
| 2009/0054526 A1 | 2/2009 | Hansen et al. |
| 2010/0311711 A1 | 12/2010 | Piomelli et al. |
| 2013/0281490 A1 | 10/2013 | Piomelli et al. |
| 2014/0094508 A1 | 4/2014 | Piomelli et al. |
| 2016/0068482 A1 | 3/2016 | Piomelli et al. |
| 2016/0068483 A1 | 3/2016 | Piomelli et al. |
| 2016/0235707 A1 | 8/2016 | Piomelli et al. |

FOREIGN PATENT DOCUMENTS

| | | |
|---|---|---|
| EP | 0 742 223 A1 | 11/1996 |
| EP | 0 742 223 B1 | 11/1996 |
| EP | 2782567 B1 | 3/2017 |

(Continued)

OTHER PUBLICATIONS

Astarita, G. et al., "Pharmacological Characterization of Hydrolysis-Resistant Analogs of Oleoylethanolamide with Potent Anorexiant Properties," The Journal of Pharmacology and Experimental Therapeutics, vol. 318, No. 2, accepted May 12, 2006.
Armirotti, Andrea et al., "β-Lactones Inhibit N-acylethanolamine Acid Amidase by S-Acylation of the Catalytic N-Terminal Cysteine," ACS Medicinal Chemistry Letters (ACS), 2012, vol. 3, No. 5, pp. 422-426.
Banker, G.S. et al. (1996). *Modern Pharmaceutics* Third Edition, Marcel Dekker, Inc. New.York, 3 pages.
Beauve, C. et al. (1999). "Synthesis, Reactivity and Biochemical Evaluation of 1,3-Substituted Azetidin-2-ones as Enzyme Inhibitors," Tetrahedron 55:13301-13320.

(Continued)

*Primary Examiner* — Antonio Galisteo Gonzalez
(74) *Attorney, Agent, or Firm* — Anson M. Nomura; Mintz, Levin, Cohn, Ferris, Glovsky and Popeo, P.C.

(57) ABSTRACT

Compounds and pharmaceutical compositions are contemplated that inhibit N-acyl-ethanolamine-hydrolyzing acid amidase (NAAA) to so increase the concentration of the substrate of NAAA, palmitoylethanolamide (PEA). NAAA inhibition is contemplated to be effective to alleviate conditions associated with a reduced concentration of PEA. Among other uses, various NAAA inhibitors are especially contemplated as therapeutic agents in the treatment of inflammatory diseases.

20 Claims, 9 Drawing Sheets

(56) References Cited

FOREIGN PATENT DOCUMENTS

| WO | WO-2009/049238 A1 | 4/2009 |
|----|-------------------|--------|
| WO | WO-2011/082285 A1 | 7/2011 |
| WO | WO-2013/078430 A1 | 5/2013 |
| WO | WO-2014/144547 A2 | 9/2014 |
| WO | WO-2014/144547 A3 | 9/2014 |
| WO | WO-2014/144836 A2 | 9/2014 |
| WO | WO-2014/144836 A3 | 9/2014 |

OTHER PUBLICATIONS

Berdyshev, E. et al. (1998). "Effects of Cannabinoid Receptor Ligands on LPS-Induced Pulmonary Inflammation in Mice," *Life Sciences* 63(8): PL125-129.

Cainelli, G. et al. (1997). "Penicillin G acylase mediated synthesis of the enantiopure (S)-3-amino-azetidin-2-one," *Tetrahedron:Asymmetry* 8(19):3231-3235.

Calignano, A. et al. (Jul. 16, 1998). "Control of pain initiation by endogenous cannabinoids," Nature 394(6690):277-281.

Calignano, A. et al. (May 11, 2001). "Antinociceptive activity of the endogenous fatty acid amide, palmityethanolamide," Eur J Pharmacol 419(2-3):191-198.

Chalker, J.M. et al. (Nov. 18, 2009). "A convenient catalyst for aqueous and protein Suzuki-Miyaura cross-coupling," J Am Chem Soc 131(45):16346-16347.

D'Agostino, G. et al. (Sep. 2007, e-published Jun. 12, 2007). "Acute intracerebroventricular administration of palmitoylethanolamide, an endogenous peroxisome proliferator-activated receptor-alpha agonist, modulates carrageenan-induced paw edema in mice," 322(3):1137-1143.

Dias et al., "Antimicrobial properties of highly fluorinated silver (I) tis (pyrazoili) borates," Journal of Inorganic Biochemistry, 2006, vol. 100, pp. 158-160.

Duranti et al., "N-(2-Oxo-3-oxetanyl)carbamic Acid Esters as N-Acylethanolamine Acid Amidase Inhibitors: Synthesis and Structure-Activity and Structure—Property Relationships," Journal of Medicinal Chemistry, May 2012, pp. A-M.

Evans, D.A. et al. (1985). "The Asymmetric Synthesis of 0-Lactam Antibiotics—I. Application of Chiral Oxazolidones in the Staudinger Reaction," *Tetrahedron Letters* 26:3783.

Fiasella, A. et al. (Jul. 2014, e-published May 14, 2014). "3-Aminoazetidin-2-one derivatives as N-acylethanolamine acid amidase (NAAA) inhibitors suitable for systemic administration," *ChemMedChem* 9(7):1602-1614.

Fleisher, D. et al. (1996). "Improved oral drug delivery: solubility limitations overcome b the use of prodrugs,"Advanced Drug Delivery Reviews 19(2):115-130.

He, G. et al. (May 23, 2011, e-published Apr. 27, 2011). "A practical strategy for the structural diversification of aliphatic scaffolds through the palladium-catalyzed picolinamide-directed remote functionalization of unactivated C(sp3)—H bonds," Angewandte Chemie Int. Ed. 50(22):5192-5196.

Higashibayashi, Shuhei et al., Synthetic studies on thiostrepton family of peptide antibiotics: synthesis of the pentapeptide segment containing dihydroxyisoleucine, thiazoline and dehydroamino acid, Tetrahedron Letters (Elsevier B.V.), 2004, vol. 45, No. 19, pp. 3707-3712.

Holt et al., "Inhibition of fatty acid amide hydrolase, a key endocannabinoid metabolizing enzyme, by analogues of ibuprofen and indomethacin," Eur J Pharmacol., Jun. 2007, 565(13):26-36, Epub Mar. 2007.

International Search Report, dated Dec. 17, 2008, for International Application No. PCT/US2008/079621, filed Oct. 10, 2008, 1 page.

International Search Report and Written Opinion, dated Feb. 28, 2013, PCT application No. PCT/US2012/066421, pp. 13.

International Search Report dated Sep. 29, 2014, for PCT Application No. PCT/US2014/029007, filed Mar. 14, 2014, 4 pages.

International Search Report dated Oct. 10, 2014, for PCT Application No. PCT/US2014/029413, filed Mar. 14, 2014, 5 pages.

Kemeny, L. et al. (2007, e-published Jan. 17, 2007). "Endogenous phospholipid metabolite containing topical product inhibits ultraviolet light-induced inflammation and DNA damage in human skin," Skin Pharmacol Physiol 20(3):155-161.

Kumar, Y et al. (2003, e-published Oct. 2, 2003). "Process for Developing 3β-[4-(S)-Arylacetylamino-4β-(2-(2-furyl)ethy ]azetidin-2-one: A Carbacephem Key Intermediate," *Org. Proc. Res. Dev.* 7(6):933-935.

Lall, Manjinder S. et al., Serine and Threonine [3—Lactones: A New Class of Hepatitis A Virus 3C Cysteine Proteinase Inhibitors, Journal of Organic Chemistry (American Chemical Society), 2002, vol. 67, No. 5, pp. 1536-1547.

Li et al., "Design and Synthesis of Potent N-Acylethanolamine-hydrolyzing Acid Amidase (NAAA) Inhibitor as Anti-Inflammatory Compounds," PLoS One, Aug. 2012;7(8):e43023.

Lohse et al., "Incorporation of a phosphonic acid isostere of aspartic acid into peptides Using Fmoc-solid phase synthesis," Tetrahedron Letters, 1998, vol. 39, Issue 15, pp. 2067-2070.

Lo Verme, J. et al. (Jan. 2005, e-published Oct. 1, 2004). "The nuclear receptor peroxisome proliferator-activated receptor-alpha mediates the anti-inflammatory actions of palmitoylethanolamide," *Mol Pharmacol* 67(1):15-19.

Lo Verme, J. et al. (Dec. 2006, e-published Sep. 22, 2006). "Rapid broad-spectrum analgesia through activation of peroxisome proliferator-activated receptor-alpha," *J Pharmacol Exp Ther* 319(3):1051-1061.

Mazzari, S. et al. (Apr. 11, 1996). "N-(2-hydroxyethyl)hexadecanamide is orally active in reducing edema formation and inflammatory hyperalgesia by down-modulating mast cell activation," Eur J Pharmacol 300(3):227-236.

Mori, Tomonori et al., "Total Synthesis of Siomycin A: Construction of Synthetic Segments," Chemistry—An Asian Journal (Wiley—VCH Verlag), 2008, vol. 3, No. 6, pp. 984-1012.

Nissen, S.E. et al. (Mar. 28, 2007, e-published Mar. 25, 2007). "Effects of a potent and selective PPAR-α agonist in patients with atherogenic dyslipidemia or hypercholesterolemia: two randomized controlled trials," JAMA 297(12):1362-1373.

Office Actions and Responses for U.S Appl. No. 13/684,017, filed Nov. 21, 2012, 110 pages.

Patani, G.A. et al. (Dec. 1996). "Bioisosterism: A Rational Approach in Drug Design," *Chem Rev* 96(8):3147-3176.

Pu et al.; Synthesis and Acylation of Salts of L-Threonine -Lactone: A route to _-Lactone Antibiotics; Journal of Organic Chemistry; vol. 56, vol. 3; pp. 1280-1283, published Feb. 1, 1991.

Pu et al.; Synthesis, Stability, and Antimicrobial Activity of (+)-Obafluorin and Related beta-Lactone Antibiotics; Journal of Organic Chemistry, vol. 59, No. 13, pp. 3642-3655 (1994).

Sasso, O. et al. (May 2012, e-published Mar. 7, 2012). "Peripheral FAAH inhibition causes profound antinociception and protects against indomethacin-induced gastric lesions," Pharmacol Res 65(5):553-563.

Saturnino et al., "Synthesis and biological evaluation of new potential inhibitors of N-acyletanolamine hydrolyzing acid amidase," Bioorganic & Medicinal Chemistry Letters, 2010, vol. 20, Issue 3, pp. 1210-1213.

Sliwa, A. et al. (2012). "12- TO 22-Membered Bridged β-Lactams as Potential Penicillin-Binding Protein Inhibitors," *Chem Asian J* 7:425-434.

Solorzano, C. et al. (Dec. 8, 2009, e-published Nov. 19, 2009). "Selective N-acylethanolamine-hydrolyzing acid amidase inhibition reveals a key role for endogenous palmitoylethanolamide in inflammation," PNAS USA 106(49):20966-20971.

Solorzano, C. et al. (Aug. 12, 2010). "Synthesis and structure-activity relationships of N-(2-oxo-3-oxetanyl)amides as N-acylethanolamine-hydrolyzing acid amidase inhibitors," J Med Chem 53(15):5770-5781.

Spetzler et al., "Preparation and application of 0-amino-serine, Ams, a new building block in chemoselective ligation chemistry," Journal of Peptide Science, 1999, vol. 5, Issue 12, pp. 582-592.

Stigers, Dannon J. et al., "Incorporation of chlorinated analogues of aliphatic amino acids during cell-free protein synthesis," Chemical Communications (Royal Soc of Chemistry), 2011, 47(6):1839-1841.

(56) References Cited

OTHER PUBLICATIONS

Tsuboi, K. et al. (Mar. 25, 2005, e-published Jan. 17, 2005). "Molecular characterization of N-acylethanolamine-hydrolyzing acid amidase, a novel member of the choloylglycine hydrolase family with structural and functional similarity to acid ceramidase," J Biol Chem 280(12):11082-11092.

Tsuboi, K. et al. (Aug. 2007). "The N-acylethanolamine-hydrolyzing acid amidase (NAAA)," Chem Biodivers 4(8):1914-1925.

Ueda et al. "A second N-acylethanolamine hydrolase in mammalian tissues," Neuropharmacology, 2005, vol. 48, pp. 1079-1085.

Valls, Nativitat et al., Synthesis of β-chloro α-amino acids: (2S,3R)- and (2S,3S)-3-chloroleucine, Tetrahedron Letters (Elsevier B.V.), 2006, vol. 47, No. 22, pp. 3701-3705.

Wang, Zheming et al., "β-Lactone probes identify a papain-like peptide ligase in *Arabidopsis thaliana*," Nature Chemical Biology (Nature Publishing Group), 2008, vol. 4, No. 9, pp. 557-563.

Written Opinion dated Dec. 17, 2008, for PCT Application No. PCT/US2008/079621, filed Oct. 10, 2008 4 pages.

Written Opinion dated Sep. 29, 2014, for PCT Application No. PCT/US2014/029007, filed Mar. 14, 2014, 6 pages.

Written Opinion dated Oct. 10, 2014, for PCT Application No. PCT/US2014/029413, filed Mar. 14, 2014, 4 pages.

Merck Manual, Fifteenth Edition, pp. 2247-2271, 1987.

Roseborough, I.E. et al. (Jan. 2004). "Prevention and treatment of excessive dermal scarring," *J Natl Med Assoc* 96(1):108-116.

FIG. 1A

| Compound | IC$_{50}$ (uM) | Compound | IC$_{50}$ (uM) |
|---|---|---|---|
| SD41 | 2.96±0.3 | URB785 | 0.70±0.1 |
| URB788 | 16±4.8 | Cbz-D-Ser | >100 |
| URB786 (rac. +/-) | >100 | Cbz-D-Ala | >100 |
| Cbz-L-Ser | >100 | Cbz-gly | >100 |
| Cbz-L-Ala | >100 | URB787 | >100 |

FIG. 1B

| Compound | IC$_{50}$ (uM) | Compound | IC$_{50}$ (uM) |
|---|---|---|---|
| URB783 | 0.42±0.02 | URB818 | 6.0±0.6 |
| URB820 | 100uM | URB819 | 3.2±0.4 |
| URB868 (Racemic) | >100 | URB822 | >100 |
| URB828 | >100 | URB863 | 49.2±15 |
| URB827 | >100 | URB784 | 15±4.7 |

| | |
|---|---|
| URB821 (Rac. +/-) | IC$_{50}$ (uM) |
|  | 11±2.2 |
| URB864 | IC$_{50}$ (uM) |
|  | 0.46±.1 |
| URB865 | IC$_{50}$ (uM) |
|  | 1.5±0.1 |
| URB866 | IC$_{50}$ (uM) |
|  | 0.16±.04 |
| URB867 | IC$_{50}$ (uM) |
|  | 1.85±0.2 |

COMPOSITIONS AND METHODS OF INHIBITING N-ACYLETHANOLAMINE-HYDROLYZING ACID AMIDASE

CROSS-REFERENCE TO RELATED APPLICATIONS

This application is a divisional of U.S. patent application Ser. No. 13/898,225, filed May 20, 2013, which is a continuation of U.S. patent application Ser. No. 12/678,060, filed Aug. 27, 2010, which is a 371 of International Patent Application No. PCT/US08/79621, filed Oct. 10, 2008, which in turn claims the benefit of U.S. Provisional Patent Application No. 60/979,304, filed Oct. 11, 2007, all of which are incorporated herein by reference in their entirety for all purposes.

STATEMENT REGARDING FEDERALLY SPONSORED RESEARCH OR DEVELOPMENT

This invention was made with government support under NIH Grant No. DA-12413, awarded by the National Institutes of Health. The Government may have certain rights in the invention.

BACKGROUND OF THE INVENTION

The field of the invention is compositions and methods relating to inhibition of N-acylethanolamine-hydrolyzing acid amidase (NAAA), and especially as it relates to treatment and prevention of pain, inflammation, and other disorders in which fatty acid ethanolamide modulation is clinically relevant.

While there are numerous compositions and methods known in the art to treat pain and/or inflammation, numerous difficulties remain. Most significantly, side effects over long administration periods and/or higher dosages often prevent successful use of such drugs. For example, certain COX-2 inhibitors have recently been implicated in adverse cardiovascular events, while aspirin-type pain medication often increases the risk of intestinal bleeding. In other examples, ibuprofen and acetaminophen tend to negatively impact hepatic function, especially at higher dosages.

Ethanolamides of long-chain fatty acids (N-acylethanolamines (NAEs)) are present in numerous lower organisms, higher organisms, and mammals with a wide variety of functions. For example, anandamide (a polyunsaturated fatty acid-type NAE), was demonstrated to have cannabimimetic activity and was reported as acting as a ligand of TRPV1 (transient receptor potential vanilloid type 1). In contrast, saturated and monounsaturated NAEs are inactive as ligands of cannabinoid receptors. However, such compounds have been reported to possess a variety of other biological activities. For example, N-palmitoylethanolamine (PEA) has anti-inflammatory, anti-nociceptive, immunosuppressive, neuroprotective, and also antioxidant activity. Interestingly, the anti-inflammatory action of N-palmitoylethanolamine could be mediated by activation of peroxisome proliferator-activated receptor-alpha (PPAR-alpha). In other examples, N-oleoylethanolamine was shown to be anorexic via PPAR-alpha (see e.g., The Journal Of Pharmacology And Experimental Therapeutics (2006), Vol. 318, No. 2, pages 563-570), and N-stearoylethanolamine to be pro-apoptotic and anorexic.

NAEs are a substrate of NAAA that catalytically hydrolyze the NAE to ethanolamine and the corresponding fatty acid. Remarkably, the catalytic activity of NAAA is significantly different from a similar enzyme, FAAH (fatty acid amide hydrolase). Among various other differences, one characteristic trait of NAAA is its activity optimum at a pH of about 5.0. NAAA also exhibits a substantial preference for N-palmitoylethanolamine (PEA) over other NAEs, is activated by TRITON X100™ (registered trademark by Union Carbide; 4-octyl-phenol polyethoxylate) and dithiothreitol (DTT). Remarkably, NAAA has lower sensitivity to inhibition with phenylmethylsulfonyl fluoride and methylarachidonyl fluorophosphonate. While the gene for NAAA has been cloned and the corresponding polypeptide is relatively well characterized (see e.g., J Biol Chem (2005), Vol. 280, No. 12, pages 11082-11092), the functional properties of NAAA in mammals are not well understood.

While numerous FAAH inhibitors have been identified in the literature (see e.g., Eur J Pharmacol (2007), 565(1-3); pages 26-36; J Enz Inhib and Med Chem (2003), 18(1), pages 55-58; Arch Biochem Biophys (1999), 362(2), pages 191-196), no inhibitors are currently reported for NAAA. Moreover, as FAAH and NAAA are not structurally closely related, it is not expected that FAAH inhibitors will provide significant inhibition of NAAA.

Therefore, while numerous compositions and methods of treating and prevention of pain and inflammation are known in the art, all or almost all of them suffer from one or more disadvantages. Consequently, there is still a need to provide improved composition and methods to treat and prevent pain and inflammation.

SUMMARY OF THE INVENTION

The present invention is directed to compositions and methods of inhibiting NAAA using various compounds contemplated and identified by the inventors. Most advantageously, such compounds and compositions will be useful in the treatment of conditions associated with a reduced level of palmitoylethanolamide, and especially inflammatory diseases.

In one preferred aspect of the inventive subject matter, a pharmaceutical composition for treatment of a condition associated with a reduced level of palmitoylethanolamide comprises a compound according to Formula I and a pharmaceutically acceptable carrier

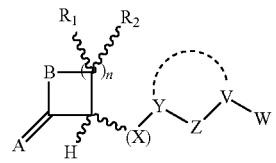

Formula I wherein A is O or S; B is O, S, or $NR^a$; $R_1$ and $R_2$ are independently H, halogen, or optionally substituted lower alkyl; n is an integer between 0 and 3; X is O, S, C(O), $NR^b$, $CHR^b$ or null; Y is C(O), C(S), or $CHR^c$; Z is O, S, $NR^d$, or $CHR^d$; V is optionally substituted lower alkyl or optionally substituted lower alkenyl; W is aryl, heteroaryl, cycloalkyl, cycloheteroalkyl, or $C(R_3R_4R_5)$, each of which may be optionally substituted; in some aspects, Y and V may form a 5- or 6-membered ring; most typically, $R^a$, $R^b$, $R^c$, and $R^d$ are independently selected from the group consisting of H, optionally substituted lower alkyl, or optionally substituted lower thioalkyl; and $R_3$, $R_4$ and $R_5$ are independently selected from the group consisting of H, optionally substituted lower alkyl, optionally substituted lower aryl, optionally substituted lower cycloheteroalkyl, and optionally substituted lower heteroaryl.

Particularly contemplated compounds include those in which A and B are O, in which X is $NR^b$ and Y is C(O) or C(S), and/or in which Z is O or $CHR^d$, V is lower alkyl, and wherein W is aryl or lower alkyl. Most preferably, n is 1, $R_1$ is H and $R_2$ is lower alkyl, and/or W is aryl or lower alkyl. Further preferred compounds include those where A is O, B is O or $NR^a$, X is $NR^b$ and Y is C(O) or C(S).

Therefore, a method of treating a patient having a condition associated with reduced levels of palmitoylethanolamide in a cell, organ, or body compartment will include a step of administering a pharmaceutical composition that includes a compound according to Formula I above. Most typically, the condition includes an inflammatory component (e.g., rheumatoid arthritis, osteoarthritis, or asthma), pain, and/or a neurodegenerative aspect. Administration of the composition is then performed under a protocol and at a dosage sufficient to reduce the inflammation in the patient. Viewed from a different perspective, contemplated methods will therefore also include in which compounds according to Formula I above will be used to inhibit NAAA. In preferred aspects, the step of contacting the NAAA is performed in vivo, and/or the compound inhibits the NAAA at an $IC_{50}$ of less than 20 microM.

Various objects, features, aspects and advantages of the present invention will become more apparent from the following detailed description of preferred embodiments of the invention.

BRIEF DESCRIPTION OF THE DRAWINGS

FIGS. 1A-1C are exemplary compounds according to the inventive subject matter and their respective $IC_{50}$ values. FIG. 1A (in order left to right, top to bottom): SD41, URB785, URB788, Cbz-D-Ser, URB786 (rac. +/−), Cbz-D-Ala, Cbz-L-Ser, Cbz-Gly, Cbz-L-Ala and URB787. FIG. 1B (in order left to right, top to bottom): URB783, URB818, URB820, URB819, URB868 (Racemic), URB822, URB828, URB863, URB827 and URB784. FIG. 1C (top to bottom): URB821 (Rac. +/−), URB864, URB865, URB866 and URB867.

FIG. 7A: Histological Score, Bax, Bcl-2; FIG. 7B: Fas Ligand, Nitrotyrosine; FIG. 7C: Par, TUNEL.

DETAILED DESCRIPTION

Figure 1C:
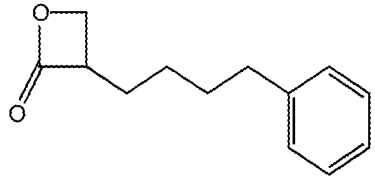
Figure 1C:
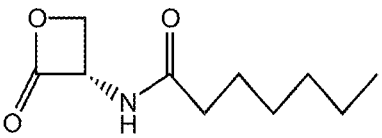
Figure 1C:
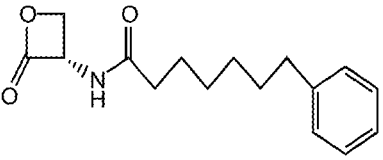
Figure 1C:
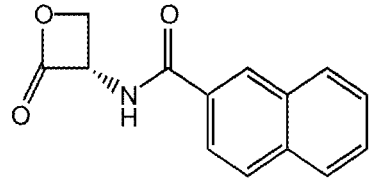
Figure 1C:
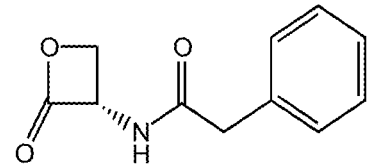

The present invention is directed to compounds, compositions, and methods of NAAA inhibition, and especially to compounds, compositions, and methods suitable for treatment of various diseases associated with reduced PEA levels in a cell, organ, or other body structure (or even the entire body). Most preferably, such modulation will result in treatment and/or prevention of pain, inflammation, and other disorders in which abnormal NAE levels are associated with a disorder. In still further contemplated aspects, the inhibitors and methods according to the inventive subject matter are also deemed useful for investigation into mechanisms and pathways in which PEA plays a regulatory or modulating role.

Contemplated Compounds

Compounds generally contemplated herein will have a structure that is effective to inhibit NAAA in competitive, non-competitive, allosteric, or other manner. Most preferably, the compounds according to the inventive subject matter will inhibit NAAA at relatively low concentrations (e.g., $IC_{50}$ equal or less than 50 microM). Among other suitable choices, especially preferred compounds have a structure according to Formula I

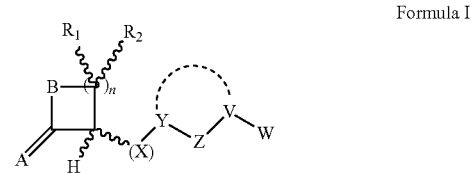

Formula I in which A is O or S; B is O, S, or $NR^a$, with $R^a$ being H, alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, N-alkyl, N-cycloalkyl, amino, thio, alkylthio, and haloalkyl (all of which may be optionally substituted); n is an integer between 0 and 3, wherein the so formed saturated or unsaturated C1-3 may be optionally and at independent locations substituted with $R_1$ and $R_2$, and wherein $R_1$ and $R_2$ are independently $R^a$ as defined above; Q is as $R^a$ as defined above; X is O, S, C(O), $NR^b$, or $CHR^b$ with $R^b$ being as $R^a$ defined above, or null; Y is C(O), C(S), or $CHR^c$ with $R^c$ being as $R^a$ defined above, or null; Z is O, S, $NR^d$, or $CHR^d$ with $R^d$ being as $R^a$ defined above, or null; V is an optionally substituted lower alkyl or an optionally substituted lower alkylene or null; W is H, aryl, heteroaryl, cycloalkyl, cycloheteroalkyl, or $C(R_3R_4R_5)$, each of which may be optionally substituted, wherein $R_3$, $R_4$ and $R_5$ are independently $R^a$ as defined above; and wherein Y and V may optionally form an optionally substituted 5-, 6-, or 7-membered ring.

In especially preferred aspects, A and B are O, and/or X is $NR^b$ and Y is C(O) or C(S). Additionally, or alternatively, it is contemplated that Z is O or $CHR^d$, V is lower alkyl, and wherein W is aryl or lower alkyl, and/or that n is 1, $R_1$ is H and $R_2$ is lower alkyl. Still further preferred compounds include those in which A is O, B is O or $NR^a$, X is $NR^b$ and Y is C(O) or C(S). In still further contemplated aspects of the inventive subject matter, X—Y may together form —CH=CH— or CH=CJ where J is halogen, especially where Z=—CHR$^d$— or null. It is still further contemplated that Y—Z—V may become Y—V by eliminating Z, or Y, by eliminating Z and V. Similarly, Z—V—W may become Z—W by eliminating V. Still further contemplated compounds include all (e.g., acidic or alkaline) hydrolytic cleavage products of the A=C—B— bond.

Still further contemplated compounds include those according to Formulae II and II as depicted below

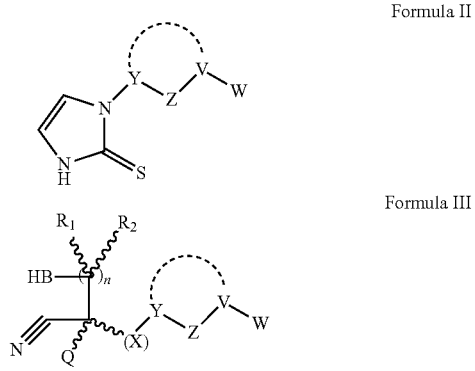

Formula II

Formula III in which B is O, S, or NR$^a$, with R$^a$ being H, alkyl, alkenyl, alkynyl, cycloalkyl, cycloalkenyl, halo, nitro, hydroxy, alkoxy, alkenyloxy, cyano, carboxy, alkoxycarbonyl, carboxyalkyl, amino, acylamino, alkylamino, dialkylamino, cycloalkylamino, N-alkyl, N-cycloalkyl, amino, thio, alkylthio, and haloalkyl (all of which may be optionally substituted); n is an integer between 0 and 3, wherein the so formed saturated or unsaturated C1-3 may be optionally and at independent locations substituted with R$_1$ and R$_2$, and wherein R$_1$ and R$_2$ are independently R$^a$ as defined above; Q is as R$^a$ as defined above; X is O, S, C(O), NR$^b$, or CHR$^b$ with R$^b$ being as R$^a$ defined above, or null; Y is C(O), C(S), or CHR$^c$ with R$^c$ being as R$^a$ defined above, or null; Z is O, S, NR$^d$, or CHR$^d$ with R$^d$ being as R$^a$ defined above, or null; V is an optionally substituted lower alkyl or an optionally substituted lower alkylene or null; W is H, aryl, heteroaryl, cycloalkyl, cycloheteroalkyl, or C(R$_3$R$_4$R$_5$), each of which may be optionally substituted, wherein R$_3$, R$_4$ and R$_5$ are independently R$^a$ as defined above; and wherein Y and V may optionally form an optionally substituted 5-, 6-, or 7-membered ring.

It should still further appreciated that where stereocenters are present, all isomers and mixtures thereof are contemplated. Similarly, where a double bond is present, the orientation of radicals at each side of the double bond may be cis or trans. FIGS. 1A-1C depict various exemplary preferred compounds according to the inventive subject matter.

As used herein, the term "halogen" refers to a fluorine, bromine, chlorine, or iodine, which is typically covalently bound to another atom (e.g., carbon). As further used herein, the term "hydroxyl" refers to a-OH group. As still further used herein, the term "carbonyl atom" refers to a carbon atom to which three atoms are covalently bound, wherein one of the three atoms is bound to the carbon atom via a double bond (which may be partially delocalized). Thus, particularly contemplated carbonyl atoms include carbon atoms in an oxo group, an aldehyde group, a carboxamide group, a carboxamidine group, and a thiocarboxamide group.

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "alkylene" as used herein refers to an alkyl having two hydrogen atoms less than the corresponding alkane (i.e., $C_nH_{2n}$). For example, suitable alkylenes include methylene groups, ethylene groups, propylene groups, etc. The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.). The term "alkaryl" as used herein refer to an alky that is covalently coupled to an aryl moiety. For example, a benzyl radical is considered an alkaryl under the definition provided herein.

Similarly, the term "alkenyl" as used herein refers to an alkyl in which at least one carbon-carbon bond is a double bond. Thus, the term "lower alkenyl" includes all alkenyls with one to ten carbon atoms. The term "cycloalkenyl" as used herein refers to a cyclic or polycyclic group containing 3 to 15 carbons and at least one double bond. Likewise, the term "alkynyl" as used herein refers to an alkyl or alkenyl in which at least one carbon-carbon bond is a triple bond. Thus, the term "lower alkynyl" includes all alkynyls with one to ten carbon atoms.

As still further used herein, the term "alkoxy" refers to a-OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or substituted cycloheteroalkyl. Similarly, the term "aryloxy" refers to a —OAr group, wherein Ar is an aryl, substituted aryl, heteroaryl, or substituted heteroaryl group.

Furthermore, the term "aryl" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

Still further, the term "substituted" as used herein means that a hydrogen atom that is covalently bound to a group or atom (or a free electron pair or electron pair of a double bond of an atom) is replaced by a covalently bound non-hydrogen substituent, including hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

The term "prodrug" as used herein refers to a modification of contemplated compounds, wherein the modified compound exhibits less pharmacological activity (as compared to the modified compound) and wherein the modified compound is converted within a target cell (e.g., B-cell) or target organ/anatomic structure (e.g., joint) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum.

On the other hand, and especially where increased solubility is desired, hydrophilic groups may be added. Still further, where contemplated compounds contain one or more bonds that can be hydrolyzed (or otherwise cleaved), reaction products are also expressly contemplated. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Moreover, especially where contemplated compounds have a higher activity when the compound is metabolized (e.g., hydrolyzed, hydroxylated, glucuronidated, etc.), it should be appreciated that metabolites of contemplated compounds are also expressly contemplated herein.

Depending on the particular purpose (e.g., analgesic, anti-inflammatory), it should be recognized that contemplated compounds may be combined (in vivo or in a pharmaceutical formulation or administration regimen) with at least one other pharmaceutically active ingredient, and especially contemplated other ingredients include various analgesics (e.g., opioids, ibuprofen-type drugs, acetaminophen-type drugs, aspirin-type drugs, etc.) various immunosuppressants and/or anti-inflammatory drugs (e.g., steroids and NSAIDS), etc. Concentrations of second pharmaceutically active ingredients are typically at or preferably below those recommended for stand-alone administration, however, higher concentrations are also deemed suitable for use herein.

Therefore, contemplated pharmaceutical compositions will especially include those in which contemplated compounds (and additional pharmaceutically active ingredients) are provided with a suitable carrier, wherein contemplated compounds are preferably present at a concentration effective to modulate fatty acid ethanolamide concentration in an organism and/or target organ to a degree effective to reduce and more preferably to treat signs and symptoms of a disease associated with an abnormal level in fatty acid ethanolamide. Viewed from a different perspective, contemplated compounds are present in a composition in an amount effective to reduce pain and/or inflammation.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. In especially preferred aspects, it is contemplated that the formulation is suitable for topical administration, administration via aerosol, and for intrathecal administration. Consequently, especially suitable formulations may be sterile aqueous solutions for topical spray or drop administration, or application as a tincture. Alternatively, suitable topical formulations include creams, ointments, foams, lotions, emulsions, etc. Furthermore, where the compound is formulated for intrathecal administration (e.g., in the treatment of spinal cord injury), it is preferred that the compound is prepared as an injectable solution, suspension, or emulsion. In still further contemplated formulations, contemplated compounds may be formulated for aerosol delivery (e.g., micropowderized, coated onto a dispersible carrier, dissolved in atomizable solvent, etc.)

It should be appreciated that the choice of the particular formulation and carrier will at least in part depend on the specific use and type of compound. There are numerous manners of drug formulation known in the art, and all of those are deemed suitable for use herein (see e.g., Pharmaceutical Preformulation and Formulation: A Practical Guide from Candidate Drug Selection to Commercial Dosage Form by Mark Gibson; Informa HealthCare, ISBN: 1574911201; or Advanced Drug Formulation Design to Optimize Therapeutic Outcomes by Robert O. Williams, David R. Taft, and Jason T. McConville; Informa HealthCare; ISBN: 1420043870).

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

For therapeutic or prophylactic purposes, contemplated compounds are ordinarily combined with one or more excipients appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

Contemplated Uses

It is generally contemplated that the compounds and compositions according to the inventive subject matter may be employed to affect any condition and/or disease associated with abnormal levels (e.g., deviation of at least 10% relative to average PEA level in healthy person at the corresponding test site) of NAEs or where modulation of normal levels of such compounds is desired for a particular purpose. Thus, and viewed from a different perspective, contemplated compounds may be used for treatment of diseases or conditions where elevation of palmitoylethanolamide levels are therapeutically desirable. Therefore, particularly contemplated conditions and diseases include those sensitive to changes of NAEs. For example, contemplated compounds and compositions may be useful in the prevention and/or treatment of pain, inflammation, cancer and metabolic diseases. Further contemplated diseases include disorders of the nervous system, and especially relating to neuroinflammation, Alzheimer's Disease, asthma, dermatitis, irritable bowel syndrome (IBS), Crohn's Disease and appetite disorders.

Therefore, conditions and diseases to be treated with contemplated compounds and compositions especially include pain, inflammation, and neurodegenerative diseases. Among other example, such diseases may include neuropathic pain, trigeminal neuralgia, postherpetic neuralgia, diabetic neuropathy, cancer pain, phantom limb pain, complex regional pain syndrome, and fibromyalgia; rheumatoid arthritis, ankolysing spondylitis, ulcerative colitis, tendonitis, psoriasis, Faber's Disease, Crohn's Disesase, rhinitis, skin allergies, asthma, and autoimmune diseases with inflammatory components such as multiple sclerosis and other demylenating disorders; Alzheimer's Disease, traumatic brain injury. Other conditions and diseases characterizable by abnormal NAE levels and for which contemplated compounds may be useful include various metabolic disorders, appetite regulation, and obesity.

Still further contemplated uses include those in which compounds and compositions according to the inventive subject matter are used for inhibition studies in vitro and in vivo to determine structure-function relationship of a compound with respect to inhibition of NAAA. Alternatively, or additionally, it should also be appreciated that contemplated compounds and compositions may be employed in various methods of inhibiting NAAA and/or activating or modulating signaling in a pathway in which PPAR-alpha is a member in signal transduction or other processing.

Synthesis of Exemplary Contemplated Compounds

URB783 was prepared from N-Boc-L-serine (1) which was cyclized in a Mitsunobu reaction to give 2, the deprotection and salification of which provided tosylate 3. The latter compound was reacted with 3-phenylpropionyl chloride to afford URB783. URB894 resulted from the reaction between 3 and 4-biphenylcarbonyl chloride, which in turn was obtained by treating 4-phenylbenzoic acid with oxalyl chloride.

(S)-(2-oxooxetan-3-yl)carbamic acid tert-butyl ester (2)

To a stirred solution of dry $PPh_3$ (72 h under vacuum in the presence of $P_2O_5$) (5 mmol) in dry $CH_3CN$ (31 mL), kept at −50° C. under $N_2$, dimethylazodicarboxylate (5 mmol) and, after 20 min, a solution of 1 (4.47 mmol) in $CH_3CN$ (10.4 mL), were added dropwise. The mixture was stirred for 1.5 h at −50/−35° C. and concentrated. Purification of the residue by flash-chromatography (cyclohexane/EtOAc 8:2 to 6:4) gave crude 2, which was finally washed and triturated to afford a white solid. Mp 120-122° C. ($Et_2O$). $[\alpha]_D^{20}$=−27° (c 0.1, $CH_3CN$). $^1H$ NMR is in accordance with literature (Arnold, et al., 1985).

(S)-2-oxooxetan-3-yl-ammonium-4-toluenesulphonate (3)

To a stirred mixture of 2 (1.34 mmol) and anhydrous p-toluenesulphonic acid (72 h under vacuum in the presence of $P_2O_5$) (1.43 mmol), kept at 0° C. under $N_2$, trifluoroacetic acid (3 mL) was added dropwise in the course of 10 min. The solution was reacted under stirring at 0° C. for 15 min, allowed to reach room temperature, and concentrated at a temperature below 30° C. The oily residue was kept under vacuum for 1 h, and the resulting white solid triturated and washed with dry diethyl ether, then kept under vacuum for 24 h. Yield 81%. Mp and $^1H$ NMR are in accordance with literature (Arnold, et al., 1988).

(S)-N-(2-oxooxetan-3-yl)-3-phenylpropionamide (URB783)

To a stirred mixture of 3 (0.4 mmol) in dry $CH_2Cl_2$ (2 mL), kept at 0° C. under $N_2$, $Et_3N$ (1.59 mmol) and 3-phenylpropionyl chloride (0.6 mmol) were added dropwise. The mixture was reacted at 0° C. for 30 min and at room temperature for 2 h, then concentrated. Purification of the residue by flash-chromatography (cyclohexane/EtOAc 1:1 to 3:7) and recrystallization gave URB783 as a white solid. Yield 60%. Mp 104-106° C. (acetone/petroleum ether). $[\alpha]_D^{20}$=−13° (c 0.5, MeOH). MS (EI): m/z 219 (M), 91 (100). IR (Nujol) 3333, 1832, 1625, 1541 $cm^{-1}$; $^1H$ NMR ($CDCl_3$) δ 2.57 (br s, 1H), 2.99 (t, 2H), 4.34 (t, 1H, J=5 Hz), 4.43 (dd, 1H, $J_1$=5 Hz, $J_2$=6.5), 5.14 (m, 1H), 5.96 (br s, 1H), 7.18-7.36 (m, 5H) ppm. $^{13}C$ NMR ($CDCl_3$): δ 31.2 ($CH_2$), 37.7 ($CH_2$), 58.4 (CH), 66.1 ($CH_2$), 126.5 (CH), 128.3 (2CH), 128.7 (2CH), 140.2, 168.4 (C=O), 172.5 (C=O) ppm.

(S)-N-(2-oxooxetan-3-yl)biphenyl-4-carboxamide (URB 894)

To a solution of biphenyl-4-carboxylic acid (2.1 mmol) in dry $CH_2Cl_2$ (5.3 mL) and dry DMF (1 mL), kept at 0° C. under $N_2$, was added oxalyl chloride (0.3 mL, 3.13 mmol). The mixture was reacted 20 min at 0° C. and 2 h at room temperature, then concentrated to give crude biphenyl-4-carbonyl chloride as a light-yellow solid. An amount of his sample (2 mmol) were dissolved in dry THF (20 mL) and the resulting solution added dropwise, at 0° C., to a suspension obtained by mixing 3 (1.3 mmol), $Et_3N$ (1.143 mL, 8.2 mmol) and dry THF (3 mL) at 0° C. under $N_2$. The ensuing mixture was reacted at 0° C. for 30 min and at room temperature for 3 h, then evaporated. Purification by flash-chromatography (cyclohexane/EtOAc 1:1) and recrystallization gave pure URB894 as an ivory coloured solid. Yield 46%. Mp 218-220° C. (acetone/petroleum ether; sealed capillary tube; decomposition of the sample with changing of colour and shrinking of the mass was noted starting from 146° C.); $[\alpha]_D^{20}$=−20° (c 0.55, $CH_3CN$). MS (EI): m/z 267 ($M^+$), 222, 181, 167 (100). IR (Nujol) 3270, 1827, 1641, 1540 cm$^{-1}$; $^1$H NMR (d$_6$-acetone) δ 4.53-4.65 (m, 2H), 4.50-4.59 (m, 1H), 7.38-7.55 (m, 3H), 7.70-7.84 (m, 4H), 8.00-8.07 (m, 2H), 8.68 (br d, 1H, J=7 Hz) ppm. $^{13}$C NMR (d$_6$-acetone): δ 58.8, 65.1, 126.9, 127.0, 128.0, 128.1, 129.0, 131.9, 139.7, 144.4, 166.4, 169.2 ppm.

EXAMPLES

Previous studies by the inventors and others have shown that the PEA produces rapid broad-spectrum analgesic effects by activating the nuclear receptor peroxisome proliferator-activated receptor alpha (PPAR-α) in both inflammatory and neuropathic pain models. More recent work has shown that PEA levels are reduced in inflamed tissues (e.g., synovial fluid from rheumatoid arthritis and osteoarthritis patients), suggesting that this bioactive lipid may participate in the modulation of the inflammatory response and/or contribute to chronic inflammatory states.

Supporting this possibility, the inventors have found that restoring PEA levels during inflammation strongly alleviates inflammation. These results suggest a novel mechanistic strategy to reduce inflammation and pain by inhibition of PEA degradation to restore normal PEA levels in inflamed tissues. In the present application the inventors have developed a class of potent and selective inhibitors of N-acylethanolamine-hydrolyzing acid amidase (NAAA), the enzyme responsible for degrading PEA.

Inflammation Reduces the Levels of Endogenous PEA

Figure 2A:
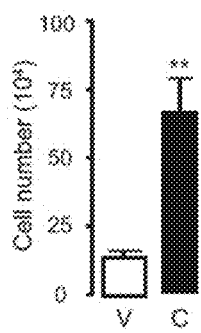
FIGS. 2A-2C are graphs illustrating the effect of inflammation on the number of infiltrating neutrophils (FIG. 2A), the levels of endogenous cellular PEA (FIG. 2B), and time course of the effect of inflammation on PEA (FIG. 2C).
Figure 2B:
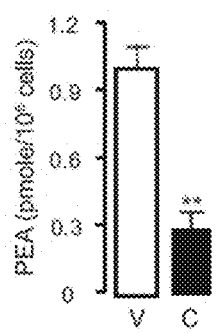
Figure 2C:
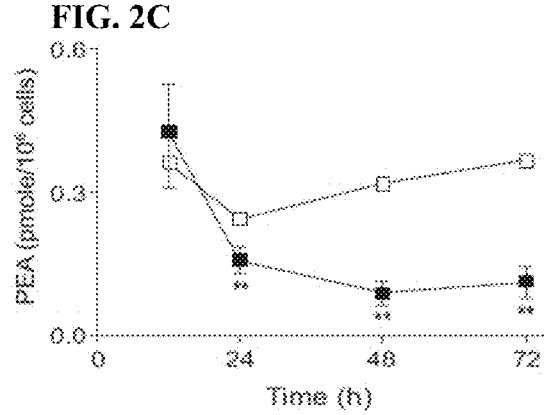

The contribution of endogenous PEA to inflammatory processes remains largely undefined. However, several lines of evidence suggest that endogenous PEA may participate in inflammation. The inventors have previously shown that the proinflammatory phorbol ester, 12-O-tetradecanoylphorbol-13-acetate (TPA), decreases dermal PEA levels following skin inflammation. These findings raised the possibility that reduced PEA levels during inflammation may allow for the progression of the inflammatory process. To further explore this idea, the inventors evaluated the effects of carrageenan-induced inflammation on PEA levels in the mouse. Polyethylene sponges injected with vehicle (10% DMSO in saline) or carrageenan (1%) were surgically implanted under the dorsal skin of mice. After 3 days, the mice were sacrificed and the sponges were removed and analyzed for inflammatory cell infiltration and cellular PEA content. In carrageenan-treated animals the number of infiltrating cells (primarily neutrophils) increased by approximately 3-fold as can be taken from FIGS. 2A-2C. Here, surgical implantation of vehicle (v) or carrageenan (c) soaked sponges under the dorsal skin of Swiss mice for 3 days (FIG. 2A) increased the number of infiltrating neutrophils and (FIG. 2B) decreased the levels of endogenous cellular PEA. (FIG. 2C) Time course of the effects of vehicle (open symbols) or carrageen (closed symbols) on PEA levels  P<0.01 or * P<0.001 vs. V, t-test or ANOVA, followed by Dunnett's post-hoc as appropriate (n=6).

Further studies revealed (data not shown) that the reduction of PEA in the inflamed tissue was at least in part due to suppression of leukocyte expression of N-acylphosphatidylethanolamine-specific phospholipase D (NAPE-PLD). NAPE-PLD-deficient mice, which produce PEA through a compensatory enzymatic route, fail to lower PEA levels in response to an inflammatory challenge and display a dampened reactivity to such challenge. Inhibitors of N-acylethanolamine-hydrolyzing acid amidase (NAAA) prevent the decrease in PEA levels and so blunt the responses induced by inflammatory stimuli. The anti-inflammatory effects of this agent are mimicked by exogenous PEA and abolished by PPAR-alpha deletion. Thus, it should be noted that the results strongly indicate that PEA activation of PPAR-alpha in leukocytes serves as an early stop signal that impedes or even inhibits the progress of inflammation.

Restoring PEA Levels with Exogenous PEA Reduces Inflammation

Figure 3A:
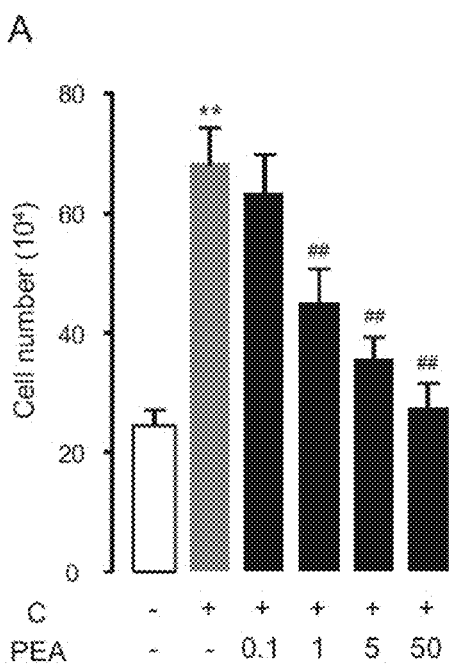
FIGS. 3A-3B are graphs illustrating the effect of exogenous PEA on the number of infiltrating neutrophils as a function of PEA concentration (FIG. 3A), and the number of infiltrating neutrophils in PPAR-alpha wild-type and null mutant mice (FIG. 3B).
Figure 3B:
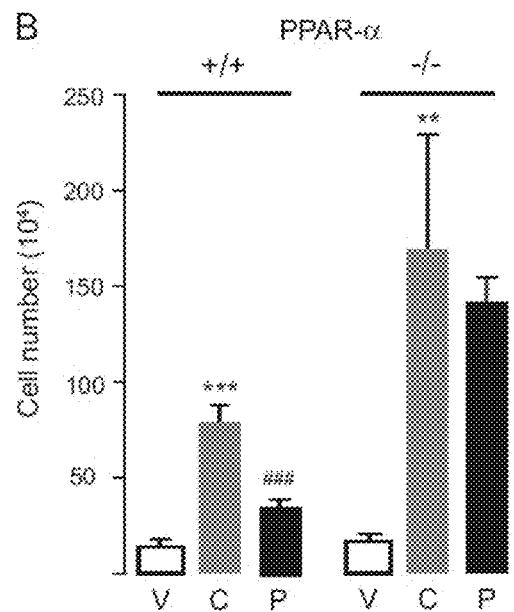

As a first step in determining the role of endogenous PEA in inflammation, the inventors examined the effects of local application of PEA on inflammatory responses. Polyethylene sponges injected with vehicle or carrageenan (1%) and either vehicle (10% DMSO in saline) or various doses of PEA (0.1-50 µg) were surgically implanted under the dorsal skin of mice. After 3 days, the mice were killed and the sponges were removed and analyzed for cell infiltration. PEA dose-dependently reduced the number of infiltrating cells as shown in FIGS. 3A-3B and edema (data not shown) in wild-type mice, but had no effect in PPAR-α-null animals. Here panels (FIGS. 3A-3B) depict the effect of vehicle (open bars), carrageenan (filled bars) or PEA (0.1-50 µg) in Swiss mice, black bars; PEA (50 µg in PPAR-α-/- mice), scored as the number of infiltrating inflammatory cells into a polyethylene sponge (size) injected with vehicle, carrageenan (1%) or PEA, implanted under the dorsal skin of (FIG. 3A) Swiss mice or (FIG. 3B) wildtype C57BL6 mice (+/+) or PPAR-α/- mice for 3 days.  P<0.01 or * P<0.001 vs. V, ## P<0.01 vs. carrageenan control. ANOVA, followed by Tukey's or Dunnett's post-hoc as appropriate (n=6). Thus, it should be appreciated that peripheral inflammation is associated with decreased PEA synthesis in infiltrating cells, and that restoring PEA levels by exogenous PEA administration reduces inflammatory responses.

Design of NAAA Inhibitors

NAAA belongs to the choloylglycine hydrolase family, which is a subgroup of the Ntn (N-terminal nucleophile) amino hydrolase superfamily. These enzymes specialize in the cleavage of linear amides and have a cysteine, serine or threonine at the first position of their aminoacidic sequence, which acts as the nucleophilic agent responsible for the catalytic attack. In the case of NAAA, the nucleophilic residue is likely Cys131. Experimental evidence suggests that the native NAAA protein undergoes a maturation process involving proteolytic cleavage of the first 130 residues, which gives a protein of 232 amino acids, where Cys131 becomes N-terminus, an event commonly observed with other Ntn hydrolases.

Figure 4:
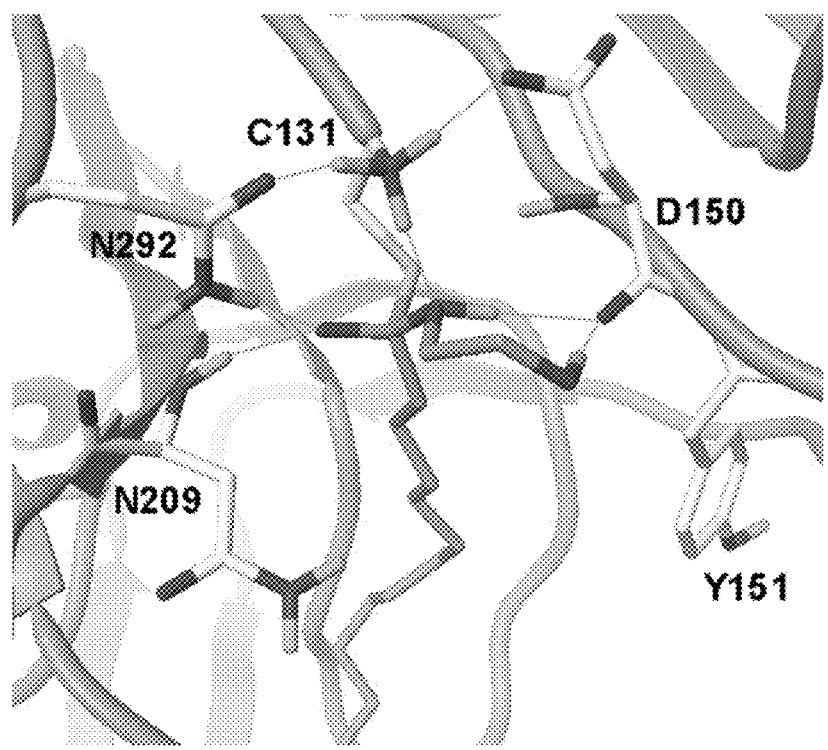
FIG. 4 is a detail view of a computer model of the active site of NAAA.
Figure 5:
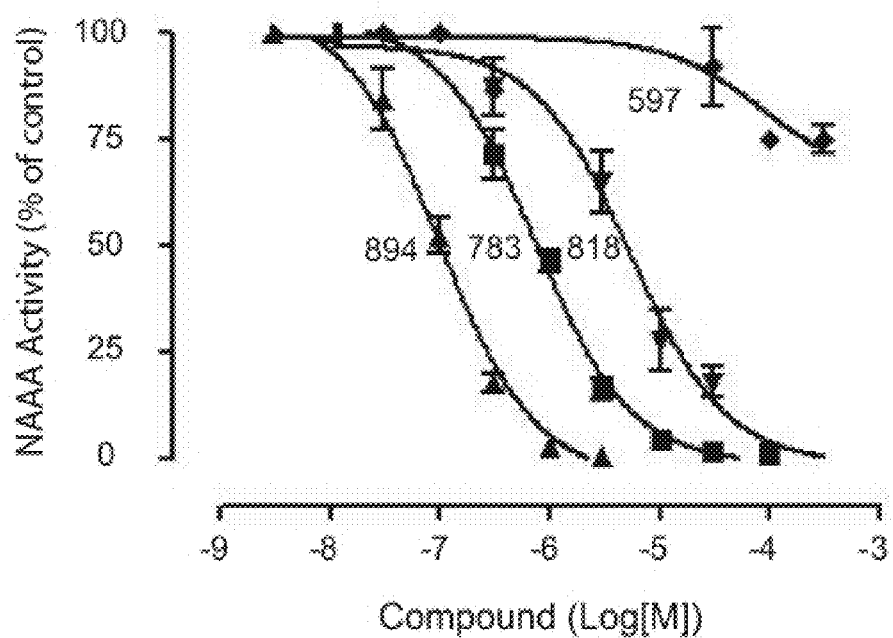
FIG. 5 is a graph depicting NAAA inhibition by selected compounds according to the inventive subject matter.

Recently, the structure of Conjugated Bile Acid Hydrolase (CBAH), a member of the Ntn family, was resolved by X-ray crystallography. An alignment of the amino acids sequences of NAAA and CBAH revealed a high degree of sequence homology between the binding sites of two enzymes. Using the coordinates of CBAH as a template, a NAAA model was built by comparative modeling. According to this model as illustrated in FIG. 4, the tetrahedral intermediate formed through attack of the catalytic nucleophile cysteine 131 on PEA is stabilized by electrostatic interactions between the carbonyl oxygen of PEA and the enzyme oxyanion hole, which is partly formed by the side-chain amide of asparagine 292 and the backbone amide of asparagine 209. In addition, a hydrophobic pocket lined by tyrosine 151, among other residues, may accommodate the flexible acyl chain of PEA.

These predictions were confirmed by site-directed mutagenesis of these amino acids lining the catalytic side. For example, replacement of Cys131, Ser133, Asp150, Tyr151 or Asn292 with alanine, completely abolished NAAA activity in vitro, whereas mutations of peripheral residues had no such effect (data not shown). Based on these results, the inventors designed a first series of NAAA inhibitors that included a hydrophobic backbone (to mimic the aliphatic fatty-acid moiety of PEA) linked to a lactone head group (to target the active cysteine residue). The inventors then synthesized and tested a number of compounds, a few of which inhibited recombinant NAAA with sub-micromolar potencies (FIGS. 1A-1C, FIG. 5). The two most potent compounds (URB783 and URB894) inhibited NAAA with $IC_{50}$ values of 420±20 nM and 115±13 nM, respectively (FIGS. 1A-1C, FIG. 5).

NAAA Inhibition Restores PEA Levels and Reduces Inflammation

Figure 6A:
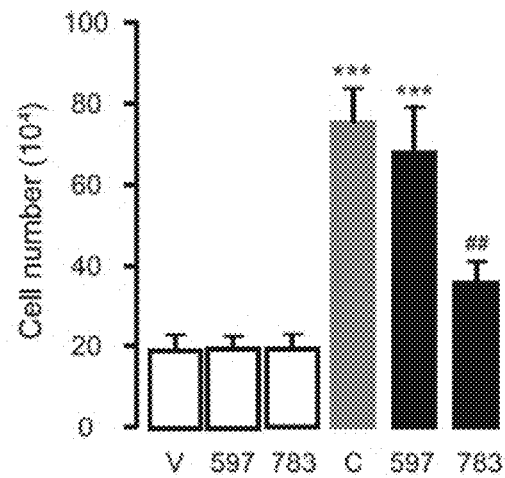
FIGS. 6A-6C are graphs illustrating the effect of an exemplary NAAA inhibitor on the number of infiltrating neutrophils (FIG. 6A), and the quantity of endogenous PEA (FIG. 6B), and the number of infiltrating neutrophils in PPAR-alpha wild-type and null mutant mice (FIG. 6C).
Figure 6B:
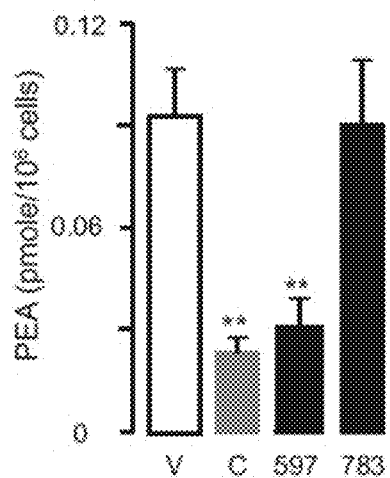
Figure 6C:
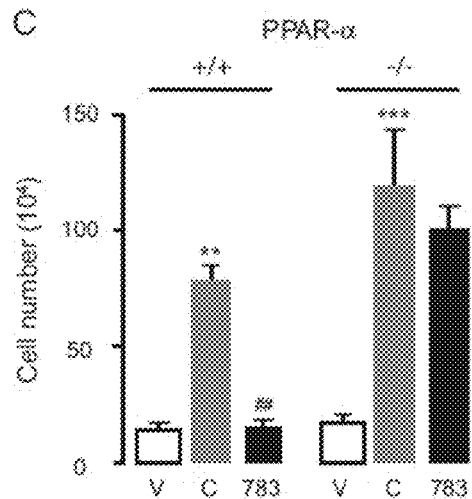

The inventors evaluated the effects of the NAAA inhibitor URB783 on inflammation, using the mouse carrageenan model. As previously shown, carrageenan exposure stimulated cell infiltration (FIG. 6A) produced edema (data not shown), and significantly reduced endogenous PEA levels (FIG. 6B). Inclusion of compound URB783, into the sponge restored PEA to basal levels (FIG. 6B) and significantly reduced the number of both infiltrating cells (FIG. 6A) and exudates volume (data not shown). Notably, the selective FAAH inhibitor URB597 had no anti-inflammatory effect in this model, suggesting that FAAH does not participate in the regulation of PEA during inflammation. The effects of compound URB783 are likely to occur through activation of PPAR-α by endogenous PEA, as these effects were absent in PPAR-α null mice (FIG. 6C) and were not reproduced by compound URB818, a chiral analog of URB783 that does not inhibit NAAA (data not shown).

More specifically, panels (A,C) illustrate inflammatory cell counts while panel (B) shows PEA levels in sponges removed from mice following 3 days of surgical implantation under the dorsal skin of (A-B) Swiss mice or (C) wildtype C57BL6 mice (+/+) or PPAR-α-knockout mice (−/−). Polyethylene sponges (1 $cm^3$) were injected with either vehicle (100 μl of water:DMSO (9:1), V, open bars), carrageenan (1%, filled bars), URB597 (30 μg), and URB783 (30 μg) as indicated.  $P<0.01$ or * $P<0.001$ vs. V, ## $P<0.01$ vs. carrageenan control. ANOVA, followed by Tukey's or Dunnett's post-hoc as appropriate (n=5-7).

NAAA Assay

Recombinant NAAA or native rat lung NAAA was incubated at 37° C. for 30 min in 0.2 ml of sodium hydrogen phosphate buffer (50 mM, pH 5.0) containing 0.1% Triton X-100, 3 mM dithiothreitol (DTT) and 50 mM heptadecenoylethanolamide as substrate. The reaction was terminated by the addition of 0.2 ml cold methanol containing 1 nmol of heptadecanoic acid (HDA, NuChek Prep, Elysian, Minn.). Samples were analyzed by LC/MS (liquid chromatography/mass spectrometry). Heptadecanoic acid was eluted on an XDB Eclipse C18 column isocratically at 2.2 ml/min for 1 min with a solvent mixture of 95% methanol and 5% water, both containing 0.25% acetic acid and 5 mM ammonium acetate. The column temperature was 50° C. ESI was in the negative mode, capillary voltage was 4 kV, and fragmentor voltage was 100 V. N2 was used as drying gas at a flow rate of 13 liters/min and a temperature of 350° C. Nebulizer pressure was set at 60 psi. [M-H]— was monitored in SIM mode using heptadecanoic acid as internal standard. Calibration curves were generated using commercial heptadecenoic acid (Nu-Chek Prep, m/z=267).

Spinal Cord Injury

In the spinal cord injury (SCI) model, extradural compression of a section of the spinal cord exposed via a four-level T5-T8 laminectomy, caused a substantial increase in iNOS expression in the inflammatory cells as well as in nuclei of Schwann cells in the white and gray matter of the spinal cord tissues collected from mice 24 hours after SCI. No iNOS staining was detected in the spinal cord obtained from sham mice. Administration of the NAAA inhibitor URB783 after SCI led to a significant reduction in the expression of iNOS as well as other markers of inflammation and cell apoptosis induced by this model, including protease-activated receptor (PAR), nitrotyrosine, Fas-ligand, Bax, Bcl-2 and Terminal Deoxynucleotidyltransferase-Mediated UTP End Labeling (TUNEL). A typical experimental protocol is described below.

Mice were randomized into 4 groups (n=40 animals/group). Sham animals were subjected to the surgical procedure except that the aneurysm clip was not applied and treated locally at the spinal cord T5-T8 level with vehicle (saline) or 3 (30 μg/mouse) 1 h and 6 h after surgical procedure. The remaining mice were subjected to SCI (as described below) and treated locally at the spinal cord T5-T8 level with vehicle (saline) or 3 (30 μg/mouse) 1 h and 6 h after SCI. The mice from each group were sacrificed at 24 h after SCI in order to collect samples for the evaluation of the parameters as described below.

Mice were anaesthetized using chloral hydrate (400 mg/kg body weight). We used the clip compression model described by Rivlin and Tator (Rivlin and Tator, 1978) and produced SCI by extradural compression of a section of the SC exposed via a four-level T5-T8 laminectomy, in which the prominent spinous process of T5 was used as a surgical guide. A six-level laminectomy was chosen to expedite timely harvest and to obtain enough SC tissue for biochemical examination. With the aneurysm clip applicator oriented in the bilateral direction, an aneurysm clip with a closing force of 24 g was applied extradurally at T5-T8 level. The clip was then rapidly released with the clip applicator, which caused SC compression. In the injured groups, the cord was compressed for 1 min. Following surgery, 1.0 ml of saline was administered subcutaneously in order to replace the blood volume lost during the surgery. During recovery from anesthesia, the mice were placed on a warm heating pad and covered with a warm towel. The mice were singly housed in a temperature-controlled room at 27° C. for a survival period of 10 days. Food and water were provided to the mice ad libitum. During this time period, the animals' bladders were manually voided twice a day until the mice were able to regain normal bladder function. Sham injured animals were only subjected to laminectomy.

Immunohistochemical localization of PAR, nitrotyrosine, FAS-ligand, Bax, Bcl-2 and iNOS. Twenty-four hours after SCI, nitrotyrosine, a specific marker of nitrosative stress, was measured by immunohistochemical analysis in the spinal cord sections to determine the localization of "peroxynitrite formation" and/or other nitrogen derivatives produced during SCI. At the 24 h after SCI, the tissues were fixed in 10% (w/v) PBS-buffered formaldehyde and 8 mm sections were prepared from paraffin embedded tissues. After deparaffinization, endogenous peroxidase was quenched with 0.3% (v/v) hydrogen peroxide in 60% (v/v) methanol for 30 min. The sections were permeabilized with 0.1% (w/v) Triton X-100 in PBS for 20 min. Non-specific adsorption was minimized by incubating the section in 2% (v/v) normal goat serum in PBS for 20 min. Endogenous biotin or avidin binding sites were blocked by sequential incubation for 15 min with biotin and avidin (DBA), respectively. Sections were incubated overnight with anti-PAR☐ (Alexis; 1:500 in PBS, v/v), anti-iNOS antibody (1:500 in PBS, v/v), anti-nitrotyrosine rabbit polyclonal antibody (Upstate, 1:500 in PBS, v/v), with anti-FAS-ligand antibody (Abcam, 1:500 in PBS, v/v), anti-Bax antibody (Santa Cruz Biotechnology, 1:500 in PBS, v/v) or with anti-Bcl-2 polyclonal antibody (Santa Cruz Biotechnology, 1:500 in PBS, v/v). Sections were washed with PBS, and incubated with secondary antibody. Specific labeling was detected with a biotin-conjugated goat anti-rabbit IgG and avidin-biotin peroxidase complex (DBA). To verify the binding specificity for nitrotyrosine, PAR, iNOS, Bax, and Bcl-2, some sections were also incubated with only the primary antibody (no secondary) or with only the secondary antibody (no primary). In these situations no positive staining was found in the sections indicating that the immunoreactions were positive in all the experiments carried out.

Terminal Deoxynucleotidyltransferase-Mediated UTP End Labeling (TUNEL) Assay was conducted by using a TUNEL detection kit according to the manufacturer's instruction (Apotag, HRP kit DBA, Milan, Italy). Briefly, sections were incubated with 15 mcg/ml proteinase K for 15 min at room temperature and then washed with PBS. Endogenous peroxidase was inactivated by 3% H2O2 for 5 min at room temperature and then washed with PBS. Sections were immersed in terminal deoxynucleotidyltransferase (TdT) buffer containing deoxynucleotidyl transferase and biotinylated dUTP in TdT buffer, incubated in a humid atmosphere at 37° C. for 90 min, and then washed with PBS. The sections were incubated at room temperature for 30 min with anti-horseradish peroxidase-conjugated antibody, and the signals were visualized with diaminobenzidine. The number of TUNEL positive cells/high-power field was counted in 5 to 10 fields for each coded slide.

Light microscopy. Spinal cord tissues were taken at 24 h following trauma. Tissue segments containing the lesion (1 cm on each side of the lesion) were paraffin embedded and cut into 5-μm-thick sections. Tissue sections (thickness 5 μm) were deparaffinized with xylene, stained with Haematoxylin/Eosin (H&E), with methyl green pyronin staining (used to simultaneously DNA and RNA) and studied using light microscopy (Dialux 22 Leitz).

Figure 7A:
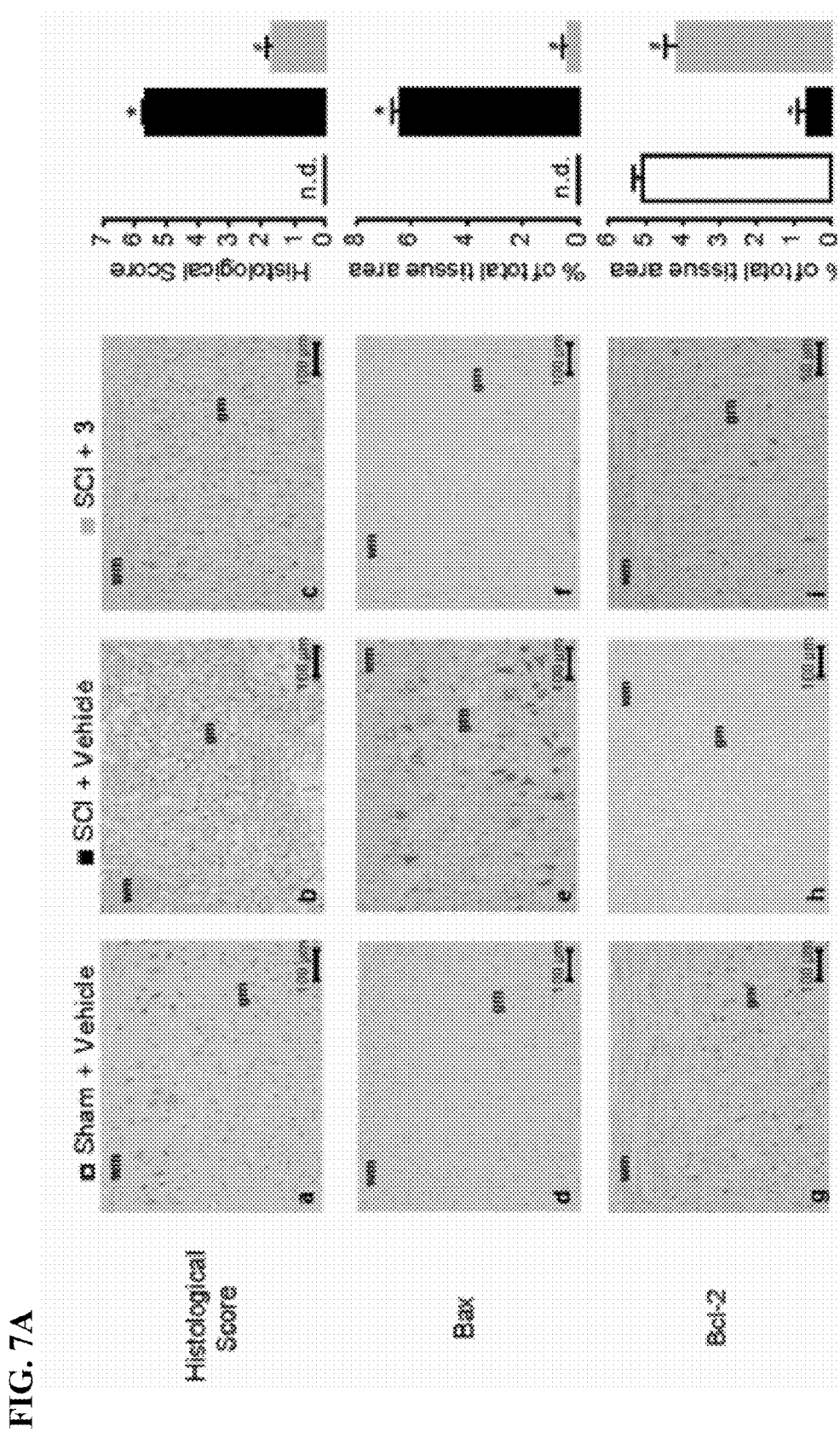
FIGS. 7A-7C depict photomicrographs of tissue sections after spinal cord injury stained with selected markers of animals treated with and without an NAAA inhibitor and control.
Figure 7B:
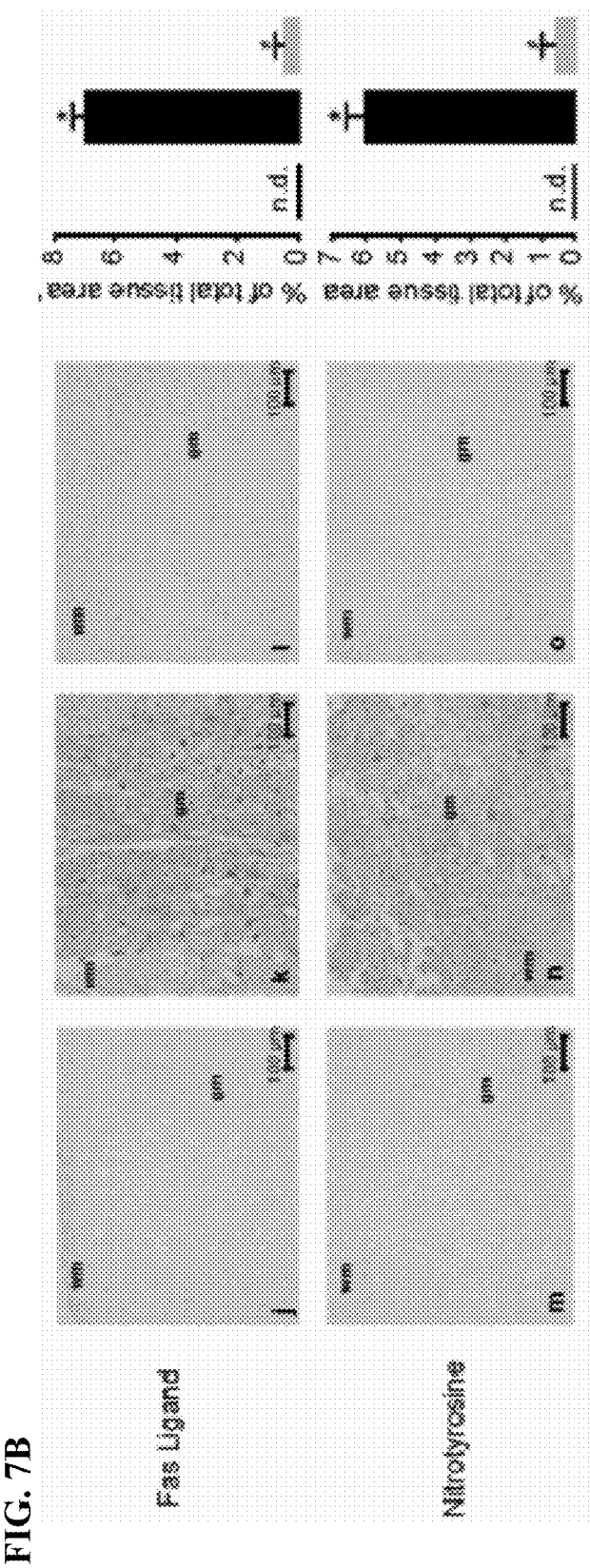
Figure 7C:
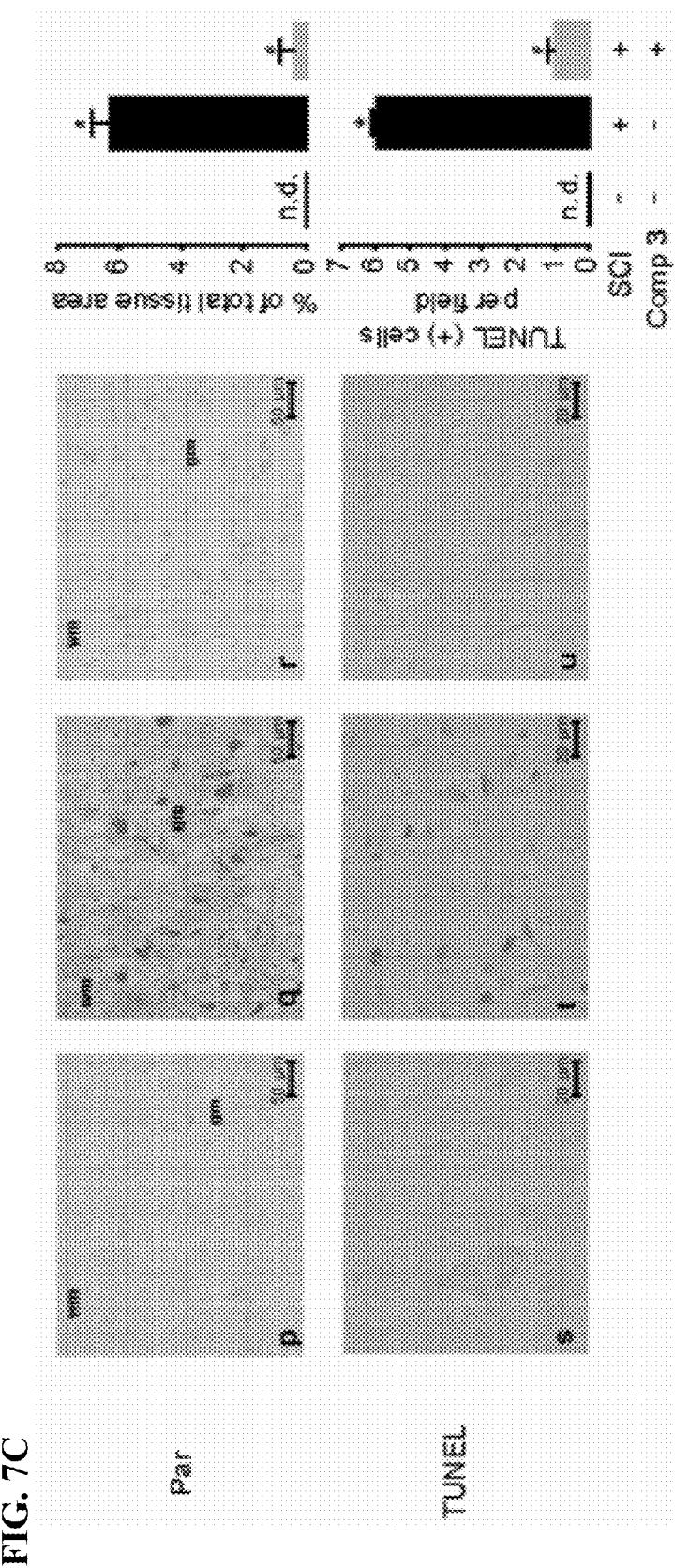

The segments of each spinal cord were evaluated by an experienced histopathologist. Damaged neurons were counted and the histopathologic changes of the gray matter were scored on a 6-point scale (Sirin et al., 2002): 0, no lesion observed, 1, gray matter contained 1 to 5 eosinophilic neurons; 2, gray matter contained 5 to 10 eosinophilic neurons; 3, gray matter contained more than 10 eosinophilic neurons; 4, small infarction (less than one third of the gray matter area); 5, moderate infarction; (one third to one half of the gray matter area); 6, large infarction (more than half of the gray matter area). The scores from all the sections from each spinal cord were averaged to give a final score for individual mice. All the histological studies were performed in a blinded fashion. FIGS. 7A-7C depict exemplary results from the experiments described above.

Thus, specific embodiments and applications of inhibiting N-acylethanolamine-hydrolyzing acid amidase have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. All extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

What is claimed is:

1. A method of treating a patient in need of increased levels of palmitoylethanolamide, comprising administering a pharmaceutical composition comprising a pharmaceutically acceptable carrier and a compound according to Formula I

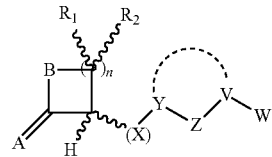

Formula I wherein

A is O; B is O, or $NR^a$; $R_1$ and $R_2$ are independently H, halogen, or optionally substituted lower alkyl; n is 1; X is $NR^b$ or $CHR^b$; Y is C(O), C(S), or $CHR^c$; Z is O, S, $NR^d$, or $CHR^d$; V is optionally substituted lower alkyl or optionally substituted lower alkenyl; wherein W is optionally substituted aryl, optionally substituted heteroaryl, optionally substituted cycloalkyl, optionally substituted cycloheteroalkyl, or $C(R_3R_4R_5)$; and wherein Y and V may optionally form a 5- or 6-membered ring;

wherein $R^a$, $R^b$, $R^c$, and $R^d$ are independently selected from the group consisting of H, optionally substituted lower alkyl, or optionally substituted lower thioalkyl; and wherein $R_3$, $R_4$, and $R_5$ are independently H, optionally substituted lower alkyl, optionally substituted lower aryl, optionally substituted lower cycloheteroalkyl, or optionally substituted lower heteroaryl.

2. The method of claim 1 wherein X is $NR^b$ and Y is C(O) or C(S).

3. The method of claim 2 wherein Z is O or $CHR^d$, V is lower alkyl, and wherein W is aryl or lower alkyl.

4. The method of claim 2 wherein W is aryl or lower alkyl.

5. The method of claim 1 wherein the patient has a condition associated with reduced levels of palmitoylethanolamide.

6. The method of claim 5 wherein the condition associated with reduced levels of palmitoylethanolamide includes an inflammatory component, and wherein administration of the composition reduces inflammation in the patient.

7. The method of claim 5 wherein the condition is rheumatoid arthritis, osteoarthritis, asthma, allergic dermatitis, psoriasis, an inflammatory bowel disease, or a spinal cord injury.

8. The method of claim 1 wherein the compound has the formula:

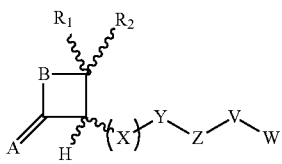

wherein

A is O; B is O, or $NR^a$; $R_1$ and $R_2$ are independently H, halogen, or optionally substituted lower alkyl; X is $NR^b$ or $CHR^b$; Y is C(O), C(S), or $CHR^c$; Z is O, S, $NR^d$, or $CHR^d$; V is optionally substituted lower alkyl or optionally substituted lower alkenyl; wherein W is optionally substituted aryl, optionally substituted heteroaryl, optionally substituted cycloalkyl, optionally substituted cycloheteroalkyl, or $C(R_3R_4R_5)$;

wherein $R^a$, $R^b$, $R^c$, and $R^d$ are independently selected from the group consisting of H, optionally substituted lower alkyl, or optionally substituted lower thioalkyl; and wherein $R_3$, $R_4$, and $R_5$ are independently H, optionally substituted lower alkyl, optionally substituted lower aryl, optionally substituted lower cycloheteroalkyl, or optionally substituted lower heteroaryl.

9. The method of claim 8 wherein $R_3$, $R_4$, and $R_5$ are independently H or lower alkyl.

10. The method of claim 8 wherein $R_3$, $R_4$, and $R_5$ are independently H.

11. The method of claim 8 wherein B is O.

12. The method of claim 8 wherein X is $NR^b$ and Y is C(O) or C(S).

13. The method of claim 8 wherein $R_1$ is H and $R_2$ is lower alkyl.

14. The method of claim 12 wherein $R_1$ is H and $R_2$ is lower alkyl.

15. The method of claim 8 wherein V is methyl, ethyl, n-propyl, n-butyl, t-butyl, i-butyl, 2-methylpropyl, cyclopropylmethyl, i-amyl, n-amyl, hexyl or optionally substituted lower alkenyl.

16. The method of claim 8 wherein V is n-amyl.

17. The method of claim 8 wherein Z is O or $CHR^d$.

18. The method of claim 8 wherein W is phenyl substituted with hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl or cyano.

19. The method of claim 8 wherein W is biphenyl.

20. The method of claim 8 wherein W is phenyl.

* * * * *